United States Patent [19]
Bochis et al.

[11] Patent Number: 5,143,918
[45] Date of Patent: Sep. 1, 1992

[54] HALOMACROLIDES AND DERIVATIVES HAVING IMMUNOSUPPRESSIVE ACTIVITY

[75] Inventors: Richard J. Bochis, East Brunswick; Matthew J. Wyvratt, Jr., Mountainside, both of N.J.

[73] Assignee: Merck & Co., Inc., Rahway, N.J.

[21] Appl. No.: 759,747

[22] Filed: Sep. 12, 1991

Related U.S. Application Data

[63] Continuation of Ser. No. 596,177, Oct. 11, 1990, abandoned.

[51] Int. Cl.$^5$ ............... A61K 31/695; A61K 31/395; C07D 498/16
[52] U.S. Cl. ................... 514/291; 514/183; 514/411; 540/456
[58] Field of Search ............... 540/456; 514/183, 411; 314/29

[56] References Cited

U.S. PATENT DOCUMENTS

| | | | |
|---|---|---|---|
| 4,650,803 | 3/1987 | Stella et al. | 514/291 |
| 4,894,366 | 1/1990 | Okuhara et al. | 540/456 |
| 4,916,138 | 4/1990 | Ueda et al. | 514/294 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 4,987,139 | 1/1991 | Chen et al. | 514/321 |
| 5,011,844 | 4/1991 | Fehr | 514/291 |
| 5,064,835 | 11/1991 | Bochis et al. | 514/291 |

FOREIGN PATENT DOCUMENTS

| | | |
|---|---|---|
| 0315978 | 5/1989 | European Pat. Off. |
| 0323042 | 7/1989 | European Pat. Off. |
| 0349061 | 1/1990 | European Pat. Off. |
| 0353678 | 2/1990 | European Pat. Off. |
| 0356399 | 2/1990 | European Pat. Off. |
| 0388152 | 9/1990 | European Pat. Off. |
| 0388153 | 9/1990 | European Pat. Off. |
| 0402931 | 12/1990 | European Pat. Off. |
| 0413532 | 2/1991 | European Pat. Off. |
| 0423714 | 4/1991 | European Pat. Off. |
| 0427680 | 5/1991 | European Pat. Off. |
| 0428169 | 5/1991 | European Pat. Off. |
| 0428365 | 5/1991 | European Pat. Off. |
| 0444659 | 9/1991 | European Pat. Off. |
| 0444829 | 9/1991 | European Pat. Off. |
| WO89/05304 | 6/1989 | World Int. Prop. O. |
| WO90/14826 | 12/1990 | World Int. Prop. O. |
| WO91/02736 | 3/1991 | World Int. Prop. O. |
| WO91/04025 | 4/1991 | World Int. Prop. O. |
| WO91/13889 | 9/1991 | World Int. Prop. O. |
| WO91/13899 | 9/1991 | World Int. Prop. O. |

OTHER PUBLICATIONS

Tanaka, et al., J. Am. Chem. Soc., 1987, 109 5031-5033.
Bierer, et al., Science, 1990, 250, 556-559.
Donald, et al., Tetrahedron Lett., 1991, 32, 1375-1378.
C. Arita, et al., Clin. exp Immunol, 1990, 82, 456-461.
N. Murase, et al., Diabetes, 1990, 39, 1584-86.
J. McCauley, et al., Lancet, 1990, 335, 674.
K. Takabayashi, et al., Clin. Immunol. Immunopathol., 1989, 51, 110-117.
M. Sakr, et al., Life Science, 1990, 47, 687-691.

Primary Examiner—Robert T. Bond
Attorney, Agent, or Firm—Charles M. Caruso; Robert J. North; J. Eric Thies

[57] ABSTRACT

Novel C-3″ and C-4″ halogen-substituted macrolides of FK-506 type structural Formula I:

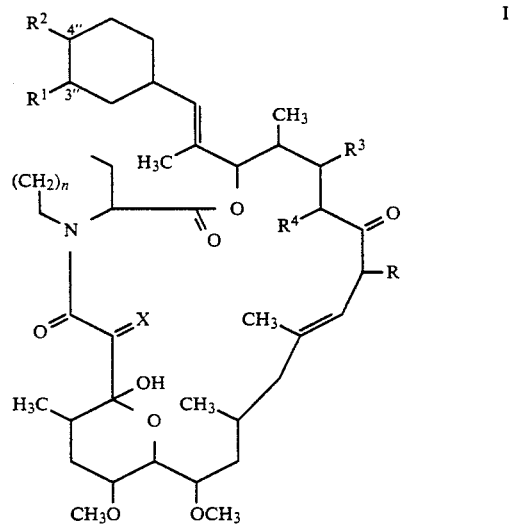

are described. These macrolide immunosuppressants are useful in a mammalian host for the treatment of autoimmune diseases (such as juvenile-onset diabetes melitus, multiple sclerosis and rheumatoid arthritis), infectious diseases and/or the prevention of rejection of foreign organ transplants, e.g. bone marrow and heart transplants. In addition, these macrolide immunosuppressants are useful in the topical treatment of inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasulitides erythemas, cutaneous eosinophilias, Lupus erythematosus or Alopecia areata.

9 Claims, No Drawings

HALOMACROLIDES AND DERIVATIVES HAVING IMMUNOSUPPRESSIVE ACTIVITY

This is a continuation of application Ser. No. 07/596,177, filed on Oct. 11, 1990 now abandoned.

The present invention is related to compounds which are useful in a mammalian host for the treatment of autoimmune diseases (such as juvenile-onset diabetes melitus, multiple sclerosis and rheumatoid arthritis), infectious diseases and/or the prevention of rejection of foreign organ transplants, e.g. bone marrow and heart transplants and are also useful in the topical treatment of inflammatory and hyperproliferative skin diseases and cutaneous manifestations of immunologically-mediated illnesses.

More particularly, this invention relates to the introduction of a halogen substituent at C-3″ or C-4″ of the cyclohexyl ring in compounds of the general structural Formula I:

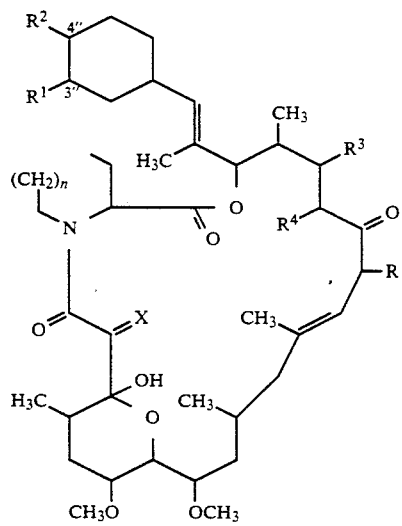

I wherein R is methyl, ethyl, propyl or allyl; $R^1$ and $R^2$ are independently halo, hydroxy, and $C_1$-$C_8$ alkoxy, with the proviso that at least one $R^1$ or $R^2$ is halogen; $R^3$ is hydrogen or hydroxy and $R_4$ is hydrogen; or $R^3$ and $R^4$ can be taken together to form a double bond; X=O or (HO, H) and n is 1 or 2. It also relates to pharmaceutical compositions containing the compounds and to a method of use of the present compounds and other agents for the treatment of autoimmune diseases, infectious diseases, the rejection of foreign organ transplants, inflammatory and hyperproliferative skin diseases and/or cutaneous manifestations of immunologically-mediated illnesses.

BRIEF DESCRIPTION OF DISCLOSURES IN THE ART

Fujisawa European and Japanese and U.S. patents (EPO Publication No. 0,184,162 and PBJ Disclosure 63-17884 U.S. Pat. No. 4,894,366) and publications (*J. Am. Chem. Soc.*, 1987, 109, 5031 and *J. Antibiotics* 1987, 40, 1249) disclose 17-allyl-1,14-dihydroxy-12-[2′-(4″-hydroxy-3″-methoxycyclohexyl)-1′-methylvinyl]-23,25-dimethoxy-13,19,21,27-tetramethyl-11,28-dioxa-4-azatricyclo-[22.3.1.0^{4,9}]octacos-18-ene-2,3,10,16-tetraone (FR-900506), 17-ethyl-1,14-dihydroxy-12-[2′-(4″-hydroxy-3″-methoxycyclohexyl)-1′-methylvinyl]-23,25-dimethoxy-13,19,21,27-tetramethyl-11,28-dioxa-4-azatricyclo[22.3.1.0^{4,9}]octacos-18-ene-2,3,10,16-tetraone (FR-900520) and related compounds which are the starting materials for the preparation of the compounds described. The synthetic preparation of the aforementioned starting material (FR-900506) has recently been reported (*J. Am. Chem. Soc.*, 1989, 111, 1157).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immuno-suppressive agents are as likely to succumb from infection as they are from their autoimmune disease.

Cyclosporin A which was approved by the U.S. FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastro-intestinal discomfort.

Newer, safer drugs exhibiting less side effects are constantly being searched for in the field.

The 23-membered tricyclo-macrolide immunosuppressant, FR-900506,

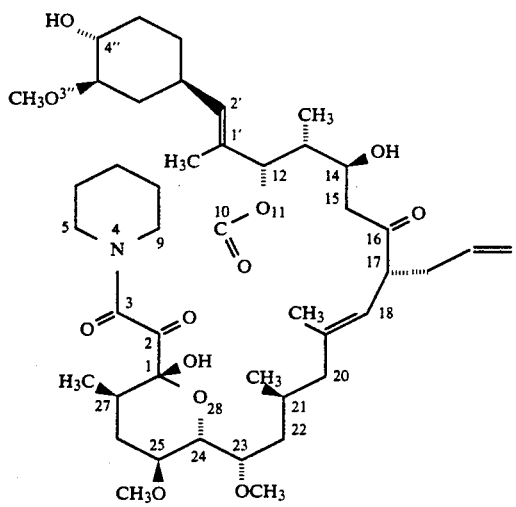

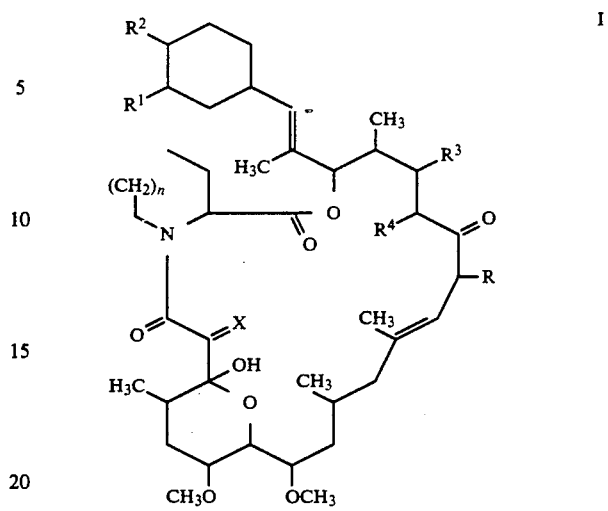

and related compounds which were isolated and characterized by Tanaka, Kuroda, and co-workers at Fujisawa Pharmaceutical Co. in Japan, see *J. Am. Chem. Soc.*, 1987, 109, 5031, and EPO Pub. No. 0,184,162 have been shown to possess exceptional immunosuppressive activity. The compound FR-900506 has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (*EPO Pub. No.* 0,315,978).

Accordingly, an object of the present invention is to provide new analogs of these tricyclomacrolides which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide analogs of these tricyclo-macrolides which possess topical activity in the treatment of inflammatory and hyperproliferative skin diseases and cutaneous manifestations of immunologically-mediated illnesses.

An additional object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory dieases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

A. Scope of the Invention

This invention relates to compounds of the general Formula I:

wherein:
R is methyl, ethyl, propyl or allyl; $R^1$ and $R^2$ are independently halo, hydroxy, $C_1-C_8$ alkoxy, with the proviso that at least one $R^1$ or $R^2$ is halogen; $R^3$ is hydrogen or hydroxy and $R_4$ is hydrogen; or $R^3$ and $R^4$ can be taken together to form a double bond; X=O or (HO, H) and n is 1 or 2;

In the present invention, compounds with asymmetric centers may occur as racemates, racemic mixtures and as individual diastereomers, with all isomeric forms of the compounds being included in the present invention.

In addition compounds with carbon-carbon double bonds may occur in Z— and E— forms with all isomeric forms of the compounds being included in the present invention.

When any variable (e.g., alkyl, R, $R^1$, $R^2$, $R^3$, $R^4$, etc.) occurs more than one time in any variable or in Formula I, its definition on each ocurrence is independent of its definition at every other occurrence.

As used herein, "alkyl" is intended to include both branched, straight chain and cycloalkyl saturated aliphatic hydrocarbon groups having the specified number of 1-8 carbon atoms, representative examples being methyl, ethyl, isopropyl, tert-butyl, sec-butyl, isopentyl, n-hexyl, n-heptyl, n-octyl, iso-octyl, and the like; "halo", as used herein, means fluoro, chloro, bromo or iodo.

In the present invention it is preferred that in compounds of Formula I:
R is ethyl, propyl or allyl;
$R^1$ is fluoro, chloro, bromo, or iodo and $R^2$ is hydroxy or methoxy; or $R^2$ is fluoro, chloro, bromo or iodo and $R^1$ is hydroxy or methoxy;
$R^3$ is hydrogen or hydroxy;
$R^4$ is hydrogen;
n is 1 or 2.

B. Preparation of Compounds Within the Scope of the Present Invention

The starting materials for the preparation of the 3"-halo and 4"-halo compounds of this invention are represented by Formula II:

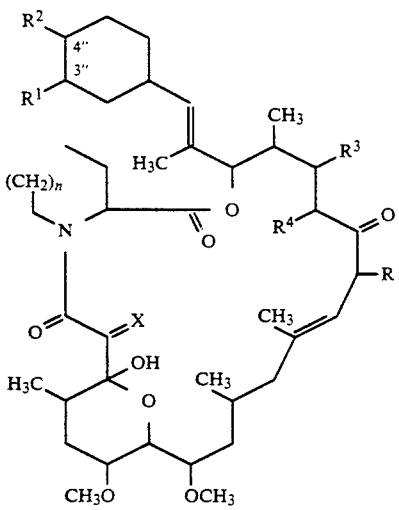

wherein R is methyl, ethyl, propyl or allyl; $R^1$ and $R^2$ are, independently, hydroxy or methoxy; $R^3$ is hydrogen or hydroxy; $R^4$ is hydrogen or $R^3$ and $R^4$ can be taken together to form a double bond. X is O; and n is 1 or 2.

The production and characterization of compounds of Formula II is well known in the literature (see EPO Publication No. 0,323,042, EPO Publication No. 0,184,162, PBJ Disclosure 63-17884, J. Am. Chem. Soc., 1987, 109, 5031 and J. Antibiotics, 1987, 40, 1249). Both biological fermentation and synthetic processes may be found. A synthetic route to compounds of Formula II can involve modifications of a route described in J. Am. Chem. Soc., 1989, 111, 1157.

Biological fermentation followed by synthetic modification is presently favored in the art as the method to produce compounds of Formula II. Organisms belonging to the genus Streptomyces such as Streptomyces tsukubaensis, No. 9993 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where R is allyl, $R^1$ is methoxy, $R^2$ and $R^3$ are hydroxyl, $R^4$ is hydrogen, X is O and n is 2; (B) where R is ethyl, $R^1$ is methoxy, $R^2$ and $R^3$ are hydroxyl, $R^4$ is hydrogen, X is O and n is 2; (C) where R is methyl, $R^1$ is methoxy, $R^2$ and $R^3$ are hydroxyl, $R^4$ is hydrogen, X is O and n is 2; and (D) where R is allyl, $R^1$ is methoxy, $R^2$ and $R^3$ are hydroxyl, $R^4$ is hydrogen, X is O and n is 1.

A lyophilized sample of the isolated Streptomyces tsukubaensis, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of R may be conveniently reduced to propyl by well known methods. The $R^2$ or $R^3$ hydroxyls may be protected by well known methods, for example as disclosed in EPO Publication 0,323,042. In addition, the hydroxy of $R^3$ may be reduced to a hydrogen or eliminated to form a double bond with $R^4$ (by methods similar to those disclosed in EPO Publication 0,323,042). The carbonyl of X may be reduced to a hydroxy by methods disclosed in EPO Publication 0,323,042 also U.S. Ser. No. 07/486,700 filed Mar. 1, 1990. The methoxy of $R^1$ as produced may be replaced with hydroxy or demethylated and subsequently protected as desired, if necessary. This demethylation of $R^1$ may be carried out in a fermentation reaction using the compounds of Formula II as a feedstock. For instance, compound B named under Formula II above may be demethylated at $R^1$ above by using the microorganism Actinomycetales ATCC No. 53771 (as taught in U.S. Ser. No. 213,025 filed Jun. 29, 1988 and hereby incorporated by reference) or produced directly by a mutant organism (as taught in U.S. Ser. No. 323,653 filed Mar. 15, 1989 and hereby incorporated by reference). Similarly, compound A may be demethylated (as taught in U.S. Ser. No. 213,063 also filed Jun. 29, 1988).

Suitable protecting groups for hydroxyl include those groups well known in the art which are: 1-(lower alkylthio) (lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributysilyl, tri-isopropylsilyl (TIPS), t-butyldimethylsilyl, (TBDMS) tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyldiphenylsilyl, and the most preferred one may be tert-butyl-dimethylsilyl, tri-i-propylsilyl and tert-butyldiphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in EPO Publication No. 0,184,162. This document is hereby incorporated by reference.

The compounds of the present invention which are represented by Formula I are prepared by the methods shown in the following Reaction Schemes wherein R, $R_1$, $R_2$, $R_3$, $R_4$, X and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

As shown in Reaction Scheme A for preparing the 4"-halogen derivatives, the C-14-oxygen-protected macrolide (V protected with TIPS or TBDMS) is prepared from the 4",14-dihydroxy macrolide (III) by treating III with silylating agents TIPSX or TBDMSX (where X=chloride or trifluoromethane sulfonate) to form IV and hydrolyzing off the C-4" protecting group to give V, and reacted with o-nitrobenzene sulfonyl chloride to form VI, which is then reacted with LiX, where X=Cl, Br, I, in an aprotic solvent, e.g., N,N- dimethylformamide, to introduce the halo substituent at the C-4" position to produce VIII. The protecting group at C-14 is then removed to produce IX. Compound V can be treated with DAST at 0° C. in $CH_2Cl_2$ and after the removal of protecting groups, if any, to give compound IX where $R_2=F$.

A route to C-3" halo substituted compounds is shown in Reaction Scheme B. The procedure is analogous to that for forming the C-4" halo derivatives.

The macrolide III is treated with the demethylating microorganism ATCC No. 53771 or ATCC No. 53828 to produce the C-4" and C-3" dihydroxy macrolide X. This is treated with one molar equivalent of protecting group reagent, such as tert-butyldimethylsilyl chloride or tri-isopropylsilyl trifluoromethanesulfonate, in $CH_2Cl_2$ with imidazole or 2,6-lutidine as an acid scavanger to produce a mixture of C-4" and C-3" mono-oxygen-protected derivatives. The C-4" Oxygen-protected derivative (XI) is separated and purified by chromatography.

Following the analogous procedure for the C-4" halo derivatives, the C-3" hydroxy is reacted with ortho-nitrobenzene-sulfonyl chloride to form XII, which is then reacted with LiX (where X=Cl, Br, I) to form the C-3" halo derivative XIII. In addition, C-3" and C-4" halo substituted compounds can be alternatively prepared as shown in Scheme C. Treatment of the demethylated natural product ($R=CH_2CH=CH_2$, $CH_2CH_2CH_3$, $CH_2CH_3$, or $CH_3$; $R_1=OH$; $R_2=OH$; $R_3=OH$, OTBDMS, OTIPS or H; $R_4=H$) with o-nitrobenzenesulfonyl chloride followed by base gives a mixture of epoxides which can be separated (XIV). Nucleophilic ring opening with LiX or $TiCl_4/TMSN_3$ affords the C-3" or C-4" halo derivative (XIII).

REACTION SCHEME A

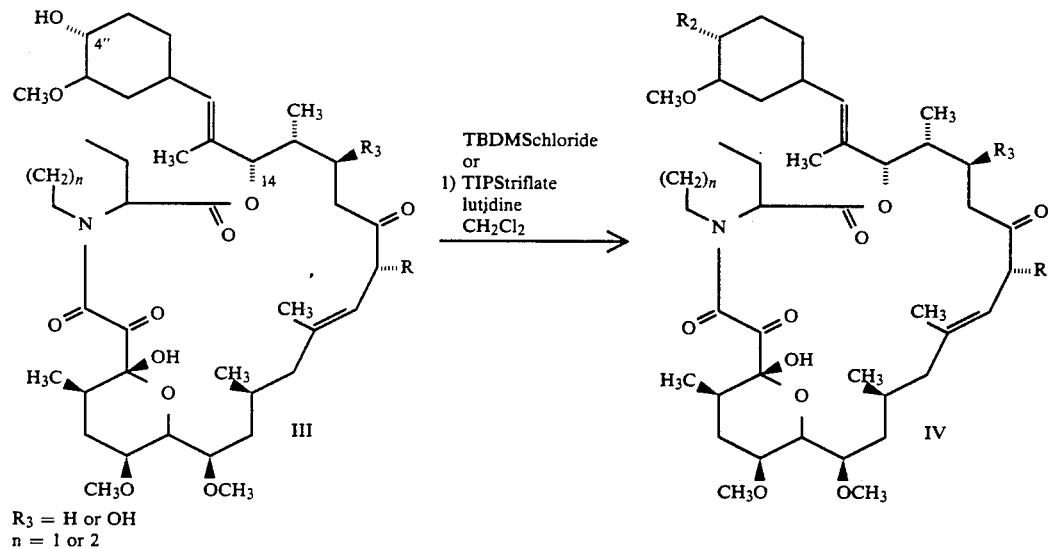

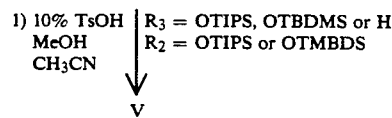

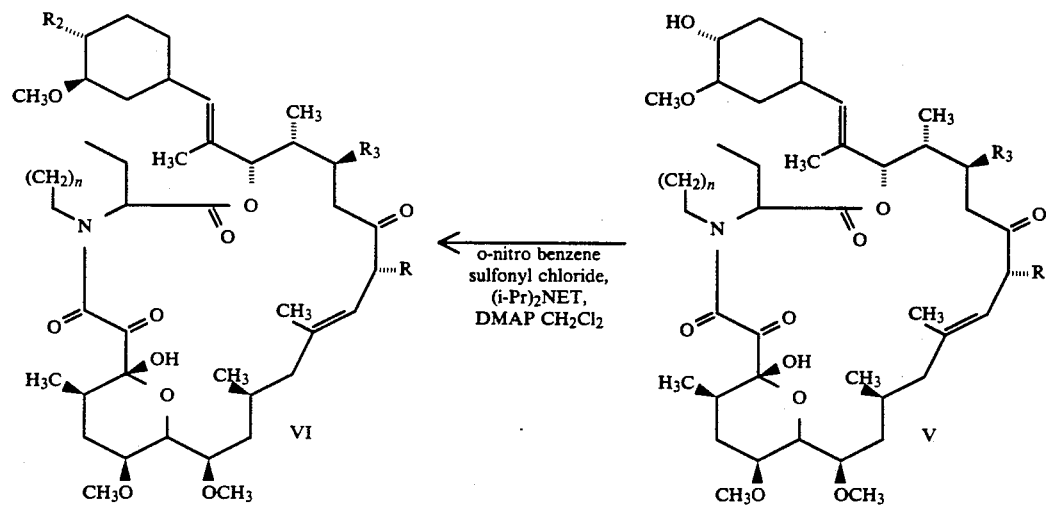

-continued
REACTION SCHEME A
R₃ = OTIPS, OTBDMS or H
R₂ = o-NO₂(C₆H₄)SO₂—O
R₃ = OTIPS, OTBDMS or H
1. DAST
   0° C., CH₂Cl₂
2. Deprotect
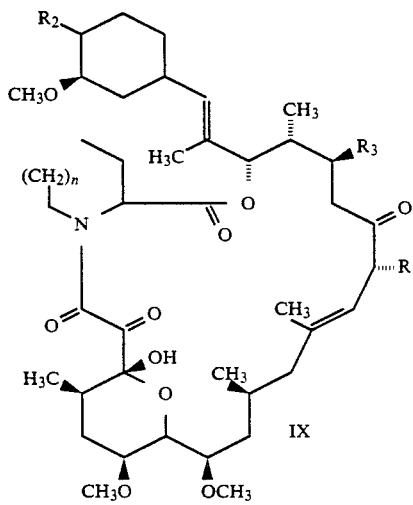
R₂ = F
R₃ = OH or H
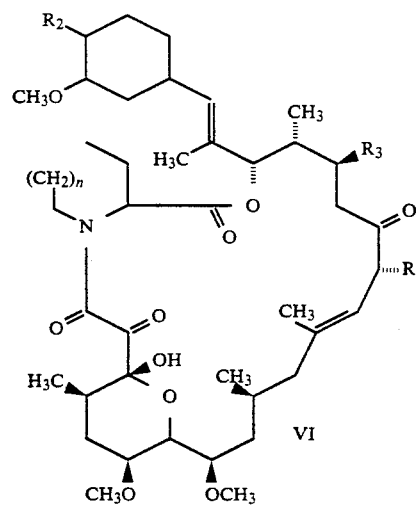
LiX
(where X = Cl, Br, I)
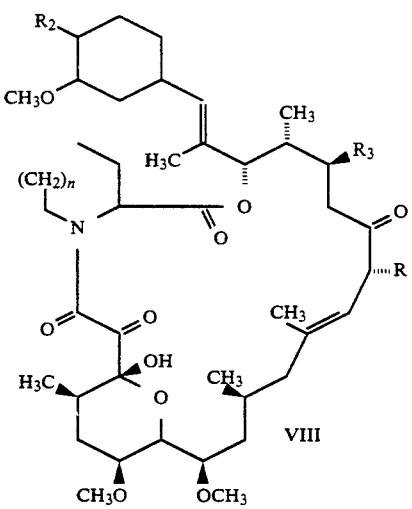
R₃ = OTIPS, OTBDMS, or H
R₂ = o-NO₂(C₆H₄)SO₂—O
n = 1 or 2
R₃ = OTBDMS, OTIPS, or H
R₂ = Cl, Br, or I
n = 1 or 2

-continued
REACTION SCHEME A
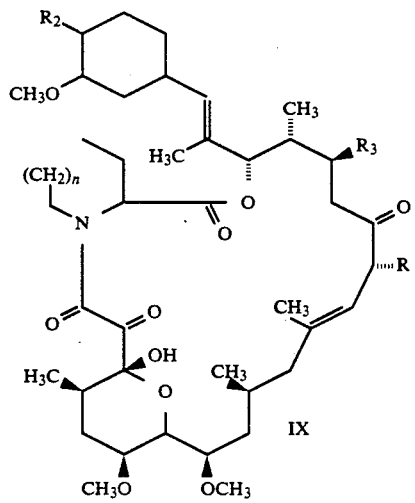
$R_3$ = OH or H
$R_2$ = Cl, Br, or I
n = 1 or 2
where
R = —$CH_2CH=CH_2$, —$CH_2CH_2CH_3$, —$CH_2CH_3$, or —$CH_3$
REACTION SCHEME B
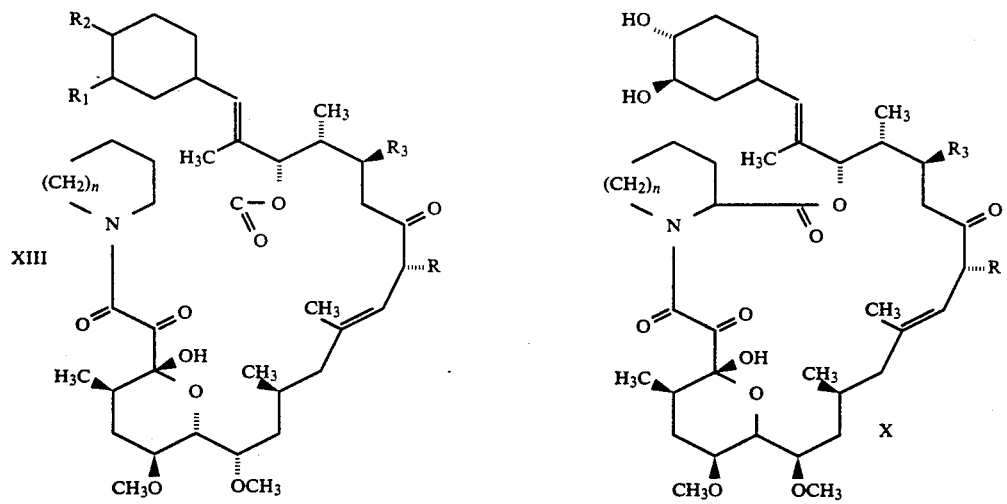
$R_1$ = F and $R_2$ = OH
or
$R_1$ = OH and $R_2$ = F
$R_3$ = OH or H
1. DAST
2. Deblock
$R^3$ = OTBDMS, OTIPS or H

REACTION SCHEME B

-continued

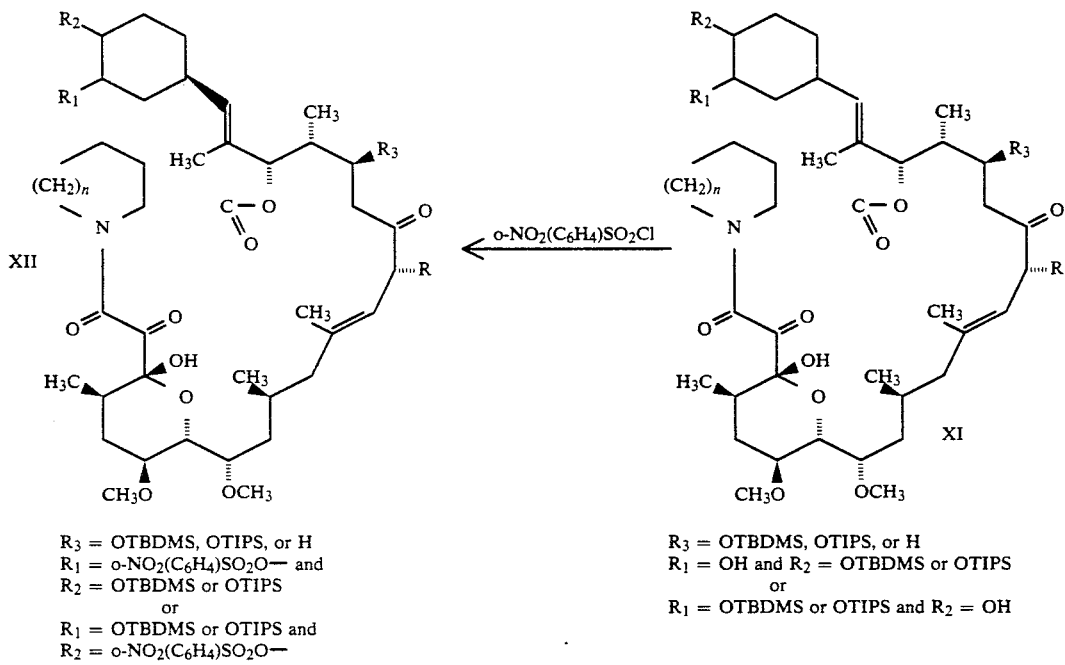

XII
R$_3$ = OTBDMS, OTIPS, or H
R$_1$ = o-NO$_2$(C$_6$H$_4$)SO$_2$O— and
R$_2$ = OTBDMS or OTIPS
or
R$_1$ = OTBDMS or OTIPS and
R$_2$ = o-NO$_2$(C$_6$H$_4$)SO$_2$O—

XI
R$_3$ = OTBDMS, OTIPS, or H
R$_1$ = OH and R$_2$ = OTBDMS or OTIPS
or
R$_1$ = OTBDMS or OTIPS and R$_2$ = OH

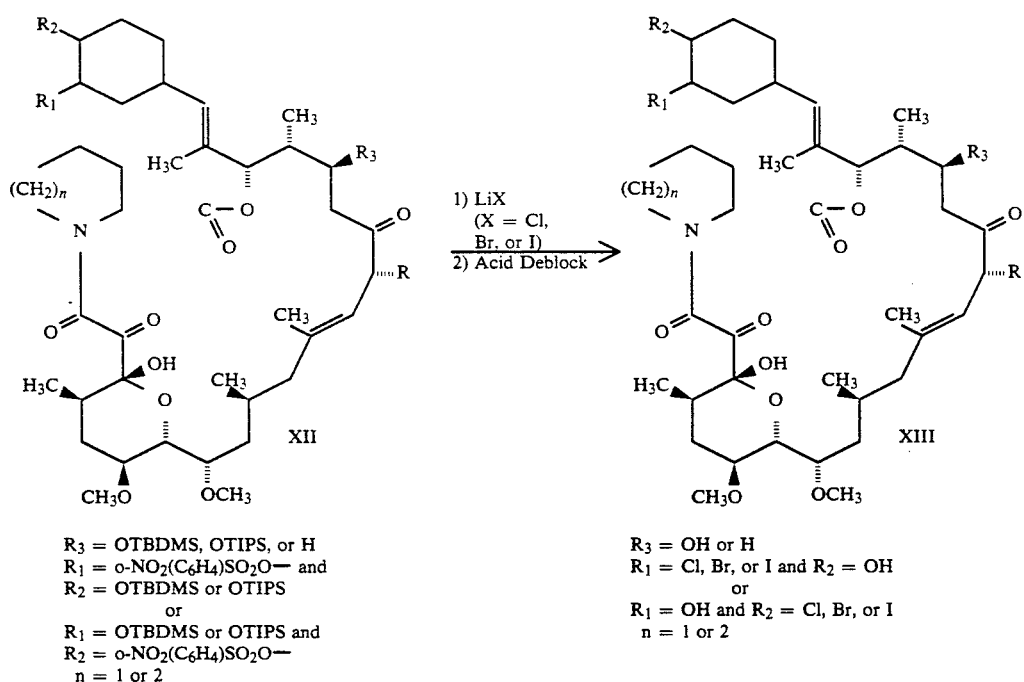

XII
R$_3$ = OTBDMS, OTIPS, or H
R$_1$ = o-NO$_2$(C$_6$H$_4$)SO$_2$O— and
R$_2$ = OTBDMS or OTIPS
or
R$_1$ = OTBDMS or OTIPS and
R$_2$ = o-NO$_2$(C$_6$H$_4$)SO$_2$O—
n = 1 or 2

XIII
R$_3$ = OH or H
R$_1$ = Cl, Br, or I and R$_2$ = OH
or
R$_1$ = OH and R$_2$ = Cl, Br, or I
n = 1 or 2 where

R = —CH$_2$CH=CH$_2$, —CH$_2$CH$_2$CH$_3$, —CH$_2$CH$_3$, or —CH$_3$ n = 1 or 2

REACTION SCHEME C

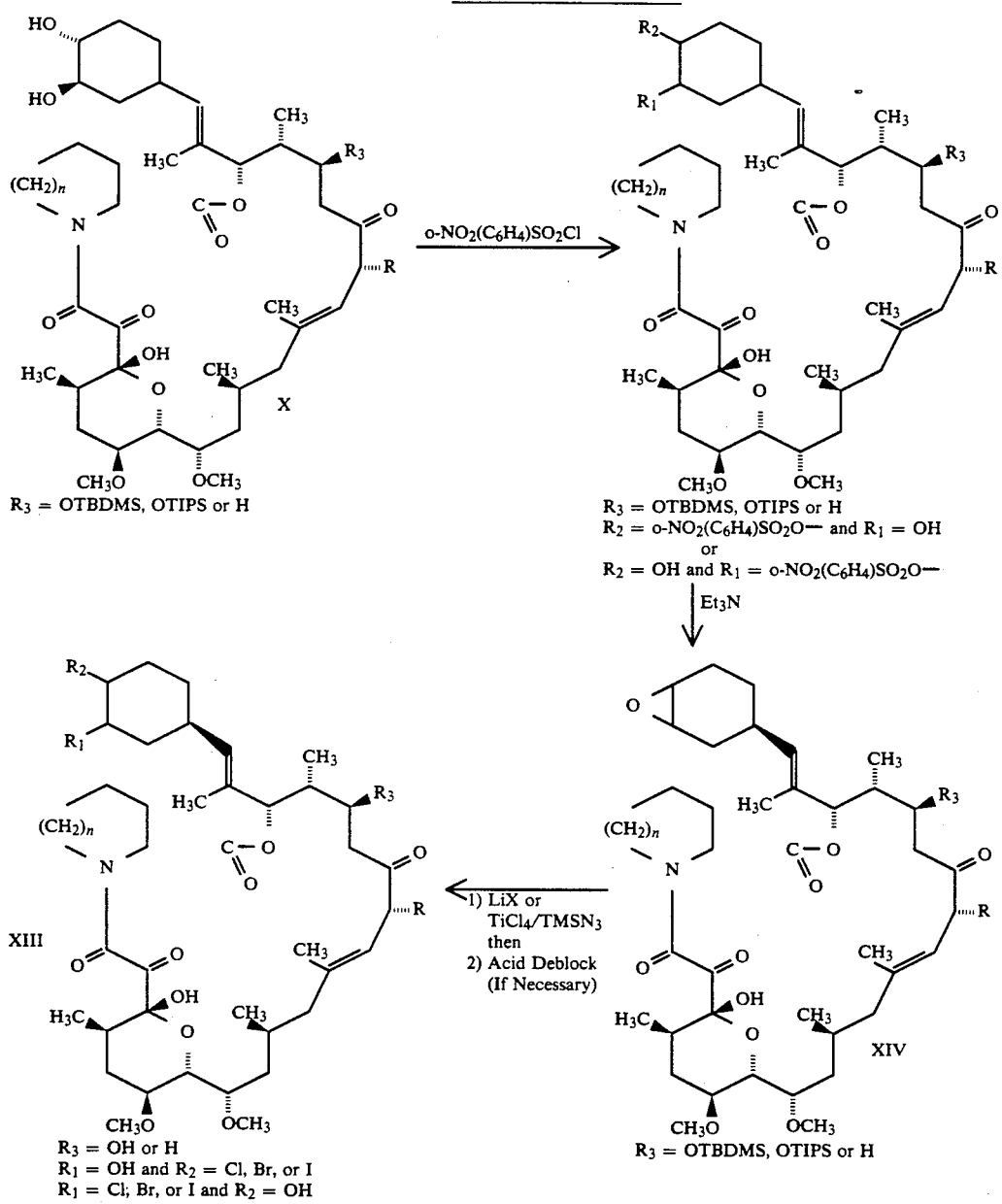

where
R = —CH₂CH=CH₂, —CH₂CH₂CH₃, —CH₂CH₃, or —CH₃

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occassionally be transformed into the other stereo isomer(s), and such cases are also included within the scope of the present invention.

In the present invention, compounds with asymmetric centers may occur as racemates, racemic mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*Tetrahedron Lett.*, 1988, 29, 277; *Tetrahedron Lett.*, 1988, 29, 281; *Tetrahedron Lett.*, 1988, 29, 4481; *J. Org. Chem.*, 1989, 54, 9; *J. Org. Chem.*, 1989, 54, 11; *J. Org. Chem.*, 1989, 54, 15; *J. Org. Chemi.*, 1989, 54, 17; *J. Am. Chem. Soc.*, 1989, 111, 1157).

C. Utility of the Compounds within the Scope of the Invention

The compounds of Formula I may be employed as immunosuppressants by methods and in dosages known in the prior art for compounds of Formula II. These compounds possess pharmacological activity, i.e., immunosuppressive activity, and the like, and therefore are useful for the treatment and prevention of the resistance to transplantation or transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, etc. The compounds of Formula I are also useful for treating inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias or Alopecia areata.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi- solid, or liquid form, and in addition auxiliary, stabilizing, thickening and coloring agents and perfumes may be used. The active object compound is included in the pharmaceutical composition in an amount sufficient to produce the desired effect upon the process or condition of diseases.

This invention also relates to a method of treatment for patients suffering from immunoregulatory abnormalities involving the administration of a compound of Formula I as the active constituent.

For the treatment of these conditions and diseases caused by immmunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixers. Compositions intended for oral use may be prepared according to any method known to the art for the manufacture of pharmaceutical compositions and such compositions may contain one or more agents selected from the group consisting of a sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by know techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapuetic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be:

(1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
   (a) a naturally-occurring phosphatide such as lecithin,
   (b) a condensation product of an alkylene oxide with a fatty acid, for example, polyoxyethylene stearate,
   (c) a condensation product of an ethylene oxide with a long chain aliphatic alcohol, for example, heptadecaethyleneoxycetanol,
   (d) a condensation product of ethylene oxide with a partial ester derived from a fatty acid and a hexitol such as polyoxyethylene sorbital monooleate, or
   (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconutoil, or in a mineral oil such as liquid paraffin. The oily suspensions may contain a thickening agent, for example, beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally, occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, gels, lotions, ointments, jellies, solutions or suspensions, etc., containing the immunoregulants are employed.

Dosage levels of the order from about 0.01 mg to about 100 mg per kilogram of body weight per day are useful in the treatment of the above-indicated conditions (from about 0.5 mg to about 5 gm per patient per day). In addition, the compounds of the present invention may be administered on an intermittent basis; i.e. at semiweekly, weekly, semi-monthly or monthyl intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient. For topical administration in larger mammals a preparation containing a 1-3% concentration of active agent may be utilized.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1-hydroxy-14-triisopropylsilyloxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A stirred solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (7.0 g, 8.84 mmol) containing 2,6 lutidine (3.7 g, 34.6 mmol) was cooled to 0° C. and treated with triisopropylsilyl trifluoromethanesulfonate (11.06 g, 36.0 mmol). After stirring at RT for 16 hr, the reaction mixture was diluted with n-hexane (400 ml). The suspension was filtered and the filtrate passed over SiO$_2$ (760 g). Elution with n-hexane/ethyl acetate (3:1) yielded 17-ethyl-1-hydroxy-14-triisopropylsilyloxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (9.18 g, 94%) as a foam. Mass Spec (C$_{61}$H$_{109}$NO$_{12}$Si$_2$)(1104.72) FAB+Li:1110 (M+Li), 745, 720, 695, 266.

EXAMPLE 2

17-Allyl-1-hydroxy-14-triisopropylsilyloxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with triisopropylsilyl trifluoromethanesulfonate as in Example 1 yields 17-allyl-1-hydroxy-14-triisopropylsilyloxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 3

17-Propyl-1-hydroxy-14-triisopropylsilyloxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-propyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with 2,6-lutidine and triisopropylsilyl trifluoromethanesulfonate in MeCl$_2$ as in Example 1 yields 17-propyl-1-hydroxy-14-triisopropylsilyloxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 4

17-Ethyl-1-hydroxy-14-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (7.0 g, 8.84 mmol) in MeCl$_2$ (150 ml) containing 2,6 lutidine (2.26 g, 23.0 mmol) was cooled to 0° C. and treated with t-butyldimethylsilyl trifluoromethanesulfonate (5.0 g, 18.9 mmol). After stirring at RT for 16 hrs, the reaction mixture was diluted with MeCl$_2$ (200 ml) and washed with 1N HCl (50 ml). The organic layer was separated and washed successively with saturated aqueous sodium bicarbonate and brine. After drying over magnesium sulfate and removal of the solvent in vacuo, the residue was chromatographed over SiO$_2$ (750 g). Elution with n-hexane/ethyl acetate (2:1) yielded 17-ethyl-1-hydroxy-14-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (6.81 g, 73%) Mass Spec: C$_{55}$H$_{97}$NO$_{12}$Si(1020.56) FAB:1042 (M+Na), 756, 678, 511, 266.

EXAMPLE 5

17-Allyl-1-hydroxy-14-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with 2,6-lutidine and t-butyldimethylsilyl trifluoromethanesulfonate in MeCl$_2$ as in Example 4 yields 17-allyl-1-hydroxy-14-t-butyldimethylsilyloxy-12-[2'-(4''-t-butyldimethylsilyloxy-3''-methoxycyclohexy-1)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 6

17-Methyl-1-hydroxy-14-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-methyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with 2,6-lutidine and t-butyldimethylsilyl trifluoromethanesulfonate in MeCl$_2$ as in Example 4 yields 17-methyl-1-hydroxy-14-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 7

17-Ethyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-Ethyl-1-hydroxy-14-triisopropylsilyloxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (8.98 g, 8.14 mmol) was slowly added to methanol (70 ml) containing p-toluenesulfonic acid monohydrate (0.70 g). The compound slowly dissolved and after 2 hr. TLC hexane/ethyl acetate (3:1) indicated no starting material was present. The reaction mixture was diluted to 250 ml with MeCl$_2$ and washed with saturated aqueous NaHCO$_3$ (250 ml). The organic layer was separated and the aqueous layer was extracted with additional MeCl$_2$. The combined organic extracts were washed with brine and dried over magnesium sulfate. After evaporation in vacuo, the residue was chromatographed over SiO$_2$ and eluted with MeCl$_2$/isopropanol (100:3) to yield 17-ethyl-1-hydroxy, 14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (6.77 g, 87.9%). Mass Spec: C$_{52}$H$_{88}$NO$_{12}$Si (948.37) FAB+Li:955 (M+Li), 721, 695, 676, 553, 266.

EXAMPLE 8

17-Allyl-1-hydroxy-14-triisopropylsilyloxy-12-[2'-(4''-hydroxy-3''-methoxycyclohexyl))-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-14-triisopropylsilyloxy-12-[2'-(4''-t riisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as in Example 7 yields 17-allyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 9

17-Methyl-1-hydroxy-14-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-methyl-1-hydroxy-1-4-t-butyldimethylsilyloxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as in Example 7 yields 17--methyl-1-hydroxy-14-triisopropylsilyloxy-12-[2'-(4'-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 10

17-Ethyl-1,14-dihydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A stirred solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3.25 g, 4.1 mmol) in MeCl$_2$ (17 ml) containing imidazole (2.55 g, 48.7 mmol) was cooled to 0° C. and treated with triisopropylsilyl trifluoromethanesulfonate (7.41 g, 24.2 mmol). The reaction mixture was allowed to warm to RT and stirred for 16 hrs. The reaction mixture was diluted with MeCl$_2$ (20 ml) and n-hexane (40 ml). The resultant suspension was filtered and the filtrate was passed over SiO$_2$. Elution with n-hexane/ethyl acetate (3:1) yielded 17-ethyl-1,14-dihydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3.35 g, 86.3%). Mass Spec: C$_{49}$H$_{83}$NO$_{12}$Si(906.29) FAB:928(M+Na), 756, 678, 511, 266.

EXAMPLE 11

17-Allyl-1,14-dihydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with imidazole and triisopropylsilyl trifluoromethanesulfonate as in Example 10 yields 17-allyl-1-hydroxy-14-triisopropylsilyloxy-12-[2'-(4''-t riisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 12

17-Propyl-1,14-dihydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with imidazole and triisopropylsilyl trifluoromethanesulfonate as in Example 10 yields 17-propyl-1-hydroxy-14-triisopropylsilyloxy-12-[2'-(4''-t riisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 13

17-Ethyl-1,14-dihydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1,14-dihydroxy-12-[2'-(4''-hydroxy-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone with imidiazole and t-butyldimethylsilyl trifluoromethanesulfonate as in Example 10 yields 17-ethyl-1,14-dihydroxy-12-[2'-(4''-t-butyldimethyl-silyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 14

17-Allyl-1,14-dihydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with imidazole and t-butyldimethylsilyl trifluoromethanesulfonate as in Example 10 yields 17-allyl-1,14-dihydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 15

17-Methyl-1,14-dihydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-methyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with imidazole and t-butyldimethylsilyl trifluoromethanesulfonate as in Example 10 yields 17-methyl-1,14-dihydroxy-12-[2'-(4"-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 16

17-Ethyl-1-hydroxy-12-[2'-(4"'-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone A solution of 17-ethyl-1,14-dihydroxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.16 mmol) in MeCl$_2$ (5.0 ml) containing triethylamine (92.2 mg, 0.91 mmol) and 4-dimethylaminopyridine (61 mg, 0.49 mmol) at 0° C., was treated with methanesulfonyl chloride (69.6 mg, 0.61 mmol). After stirring at RT for 2.5 hr, the reaction mixture was diluted with MeCl$_2$ (10 ml) and water. The aqueous layer was separated and extracted with additional MeCl$_2$. After drying over magnesium sulfate, the solvent was removed in vacuo. The residue was chromatographed over SiO$_2$ (10 g). Elution with n-hexane/ethyl acetate (3:1) yielded 17-ethyl-1-hydroxy-1-2-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone (86.6 mg, 58%). Mass Spec: C$_{52}$H$_{89}$NO$_{11}$Si (930.36) FAB+Li:1090 (M$^+$+Li+MATRIX) 936 (M+Li).

EXAMPLE 17

17-Allyl-1-hydroxy-12-[2'-(4"'-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone A solution of 17-allyl-1,14-dihydroxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with triethylamine, 4-dimethylaminopyridine and methanesulfonyl chloride in MeCl$_2$ as in Example 16 yields 17-allyl-1-hydroxy-1-2-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone.

EXAMPLE 18

17-Propyl-1-hydroxy-12-[2'-(4"'-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone A solution of 17-propyl-1,14-dihydroxy-12-[2'-(4"-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with triethylamine, 4-dimethylaminopyridine and methanesulfonyl chloride in MeCl$_2$ as in Example 16 yields 17-propyl-1-hydroxy-1-2-[2'-(4"'-triisopropylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone.

EXAMPLE 19

17-Ethyl-1-hydroxy-12-[2'-(4"'-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone A solution of 17-ethyl-1,14-dihydroxy-12-[2'-(4'-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with triethylamine, 4-dimethylaminopyridine and methanesulfonyl chloride in MeCl$_2$ as in Example 16 yields 17-ethyl-1-hydroxy-12-[2'-(4"-t-butyldimethylsilyloxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-14,18-diene-2,3,10,16-tetraone. Mass Spec: C$_{49}$H$_{81}$NO$_{11}$Si(888.28) FAB:910 (M+Na), 870, 678,266.

EXAMPLE 20

17-Allyl-1-hydroxy-12-[2'-(4"'-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone A solution of 17-allyl-1,14-dihydroxy-12-[2'-(4'-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with triethylamine, 4-dimethylaminopyridine and methanesulfonyl chloride in MeCl$_2$ as in Example 16 yields 17-allyl-1-hydroxy-12-[2'-(4"-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-14,18-diene-2,3,10,16-tetraone.

EXAMPLE 21

17-Methyl-1-hydroxy-12-[2'-(4"'-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone A solution of 17-methyl-1,14-dihydroxy-12-[2'-(4'-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with triethylamine, 4-dimethylaminopyridine and methanesulfonyl chloride in MeCl$_2$ as in Example 16 yields 17-methyl-1-hydroxy-12-[2'-(4"-t-butyldimethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone.

EXAMPLE 22

17-Ethyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone in toluene containing a catalytic amount of acetic acid is treated with a catalytic amount of tetrakis(triphenylphosphine)palladium(0). After 5 minutes, 1.1 equivalents of tri-n-butyltin hydride is added and the reaction is stirred at RT until the proton NMR of an aliquot indicates that the reaction is complete. After quenching the reaction mixture with water and extraction with ether, the ether extracts are washed with brine and dried over magnesium sulfate. Chromatography of the residue over SiO$_2$ yields 17-ethyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. Alternatively, the enone can be reduced by dissolving this material (350 mg) and 15 mg of 5% Rh/C in 10 ml of ethanol or ethyl acetate and stirring under a hydrogen atmosphere. When the reaction is complete (tlc and/or $^1$H NMR), the mixture is filtered through diatomaceous earth, concentrated and the residue subjected to flash chromatography (75% CH$_2$Cl$_2$: 5% MeOH: 20% n-hexane) to give 294 mg of the titled compound.

EXAMPLE 23

17-Allyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reduction of 17-allyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone with tetrakis(triphenylphosphine)palladium(0) in toluene with tri-n-butyltin hydride as in Example 22 yields 17-allyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 24

17-Propyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reduction of 17-propyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone with tetrakis(triphenylphosphine)palladium(0) in toluene with tri-n-butyltin hydride as in Example 22 yields 17-propyl-1-hydroxy-12-[2'-(4''-triisopropylsilyloxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

EXAMPLE 25

17-Ethyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reduction of 17-ethyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone with tetrakis(triphenylphosphine)palladium(0) in toluene with tri-n-butyltin hydride as in Example 22 yields 17-ethyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

EXAMPLE 26

17-Allyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reduction of 17-allyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone with tetrakis(triphenylphosphine)palladium(0) in toluene with tri-n-butyltin hydride as in Example 22 yields 17-allyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

EXAMPLE 27

17-Methyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reduction of 17-methyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone with tetrakis(triphenylphosphine)palladium(0) in toluene with tri-n-butyltin hydride as in Example 22, yields 17-methyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 28

17-Ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-ethyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with p-tolunesulfonic acid as in Example 7 yields 17-ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 29

17-Allyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-allyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with p-tolunesulfonic acid as in Example 7 yields 17-allyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 30

17-Propyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The treatment of 17-propyl-1-hydroxy-12-[2'-(4''-t-butyldimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with p-tolunesulfonic acid as in Example 7 yields 17-propyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 31

17-Ethyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone(1.0 g, 1.06 mmol) in MeCl$_2$(20 ml) containing 4-dimethylaminopyridine (312 mg, 2.55 mmol) and diisopropylethylamine (319 mg, 2.47 mmol) was treated with o-nitrobenzenesulfonyl chloride (476 mg, 2.14 mmol). After stirring at RT for 18 hr, the reaction mixture was diluted with MeCl$_2$ (20 ml). The resultant suspension was filtered and the filtrate passed over SiO$_2$ (90 g). Elution with n-hexane/ethyl acetate (1:1) yielded 17-ethyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (933 mg, 78%) and starting material (206 mg, 20%).

EXAMPLE 32

17-Allyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with o-nitrobenzenesulfonyl chloride as in Example 31 yields 17-allyl-1-hydroxy--14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

Mass Spec: $C_{55}H_{86}N_2O_{16}Si$ (1091.45) FAB: 1113(M+Na), 678, 511, 266.

EXAMPLE 33

17-Propyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with o-nitrobenzenesulfonyl chloride as in Example 31 yields 17-propyl-1-hydroxy--14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 34

17-Ethyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with o-nitrobenzenesulfonyl chloride as in Example 31 yields 17-ethyl-1-ethyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 35

17-Allyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with o-nitrobenzenesulfonyl chloride as in Example 31 yields 17-allyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 36

17-Propyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with o-nitrobenzenesulfonyl chloride as in Example 31 yields 17-propyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 37

17-Ethyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (222 mg, 0.2 mmol) in dimethylformamide (12 ml) under N$_2$ atmosphere, was treated with lithium chloride (130 mg, 3 mmol) and heated at 70° C. After 5 hr, the reaction mixture was cooled, diluted with H$_2$O (90 ml) and extracted with diethyl ether (3×100 ml). The combined ether extracts were washed five times with water, dried over magnesium sulfate and evaporated in vacuo. Thin layer preparative chromatography on SiO$_2$ [n-hexane/ethyl acetate (1:1)] yielded 17-ethyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (134 mg).

Mass Spec C$_{52}$H$_{28}$ClNO$_{11}$Si(996.82) FAB: 997 (M+1), 965, 720, 694, 676, 553.

EXAMPLE 38

17-allyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with lithium chloride as in Example 36 yields 17-allyl-1-hydroxy,14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 39

17-Propyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with lithium chloride as in Example 36 yields 17-propyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 40

17-Ethyl-1-hydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with lithium chloride as in Example 8 yields 17-ethyl-1-hydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 41

17-Allyl-1-hydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with lithium chloride as in Example 36 yields 17-ethyl-1-hydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 42

17-Propyl-1-hydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with lithium chloride as in Example 36 yields 17-propyl-1-hydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 43

17-Ethyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (250 mg, 0.22 mmol) in diemthylformamide (5 ml) under N$_2$ atmosphere was treated with lithium bromide (97 mg, 1.12 mmol) and heated at 70°. After 5 hr, the reaction mixture was cooled, diluted with water (60 ml) and extracted with diethyl ether (3×75 ml portions). The combined ether extracts were washed 5 times with water, dried over magnesium sulfate and evaporated in vacuo. The residue was passed over SiO$_2$ (15 g) and eluted with n-hexane-ethyl acetate (1:1) to yield 17-ethyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (192 mg, 83%).

Mass Spec: C$_{52}$H$_{88}$BrNO$_{11}$Si(1011.28) FAB: 1011(M+1), 694, 676, 553.

EXAMPLE 44

17-Allyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-14-triisopropylsilylloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with lithium bromide as in Example 43 yields 17-allyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 45

17-Propyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-14-triisopropylsilyloxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with lithium bromide as in Example 43 yields 17-propyl-1-hydroxy,14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 46

17-Ethyl-1-hydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone with lithium bromide as in Example 43 yields 17-ethyl-1-hydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 47

17-Allyl-1-hydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone with lithium bromide as in Example 43 yields 17-allyl-1-hydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 48

17-Propyl-1-hydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-12-[2'-(4''-o-nitrobenzenesulfonyloxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone with lithium bromide as in Example 42 yields 17-propyl-1-hydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 49

17-Ethyl-1-hydroxy-14-triisopropylsilyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (4.0 g, 4.2 mmol) in dimethylformamide (30 ml) under an N$_2$ atmosphere, was treated with methyltriphenoxyphosphonium iodide (3.81 g, 8.43 mmol) and stirred at RT for 5 hr. The reaction mixture was diluted with H$_2$O (250 ml) and extracted with diethyl ether (1×200 ml, 3×100 ml). The combined extracts were washed with H$_2$O (5×100 ml). The organic extracts were dried over MgSO$_4$ and evaporated in vacuo at RT. The residue was passed over SiO$_2$ (600 g)

[n-hexane/ethyl acetate (3:1)] to yield 17-ethyl-1-hydroxy-14-triisopropylsilyloxy-12-[2'-(4''-beta iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3.30 g, 74%).

Mass Spec: C$_{52}$H$_{88}$INO$_{11}$Si (1058.27) FAB:1080(M+Na), 720, 676, 266.

EXAMPLE 50

17-Allyl-1-hydroxy-14-triisopropylsilyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with methyltriphenoxyphosphonium iodide as in Example 49 yields 17-allyl-1-hydroxy-14-triisopropylsilyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 51

17-Propyl-1-hydroxy-14-triisopropylsilyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-propyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with methyltriphenoxyphosphonium iodide as in Example 49 yields 17-propyl-1-hydroxy-14-triisopropylsilyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 52

17-Methyl-1-hydroxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The reaction of 17-methyl-1-hydroxy-12-[2'-[4'''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (500 mg, 0.64 mmol) with methyltriphenoxyphosphonium iodide (0.582 mg, 1.28 mmol) in dimethyl formamide (2.0 ml) as in Example 49 yielded 17-methyl-1-hydroxy-12-[2'-(4''-beta-iodo-3''-methoxycyclohexyl)-1'-methylvinyl]-23,25-dimethoxy-13,19,21,27-tetramethyl,11,28-dioxa-4-azatricyclo[22.3.1.04,9]octacos-18-ene-2,3,10,16-tetraone.

Mass Spec: C$_{43}$H$_{68}$INO$_{10}$ (885.93) FAB:908 (M+Na), 868,701.

EXAMPLE 53

17-Ethyl-1,14-dihydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.103 mmol) in acetonitrile (14.4 ml) was treated with 48% aqueous hydrofluoric acid (41 ml). The reaction mixture was stirred for 2 hr at RT, poured onto aqueous sodium bicarbonate and extracted with ethyl acetate. The combined organic extracts were washed with water, dried over magnesium sulfate and evaporated in vacuo. Preparative thin layer chromatography of the residue on SiO$_2$ and elution with n-hexane/ethyl acetate (1:1) yielded 17-ethyl-1,14-dihydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (31 mg, 37%) as well as starting material (26 mg, 26%).

EXAMPLE 54

17-Allyl-1,14-dihydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Treatment of 17-allyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with aqueous 48% hydrofluoric acid in acetonitrile as in Example 53 yields 17-allyl-1,14-dihydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 55

17-Propyl-1,14-dihydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Treatment of 17-propyl-1-hydroxy-14-triisopropylsilyloxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with aqueous 48% hydrofluoric acid in acetonitrile as in Example 53 yields 17-propyl-1,14-dihydroxy-12-[2'-(4''-beta-chloro-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 56

17-Ethyl-1,14-dihydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reaction of 17-ethyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos- 18-ene-2,3,10,16-tetraone (71 mg, 0.07 mmol) in acetonitrile (7.5 ml) and aqueous 48% hydrofluoric acid (2.2 ml) as in Example 53 yielded 17-ethyl-1,14-dihydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (28 mg, 46%).

Mass Spec: $C_{43}H_{68}BrNO_{11}$ (854.93) EI:855, 837, 835, 819, 817, 564, 493.

EXAMPLE 57

17-Allyl-1,14-dihydroxy-12-[2'-(4'''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reaction of 17-allyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone in acetonitrile and aqueous 48% hydrofluoric acid as in Example 53 yields 17-allyl-1,14-dihydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 58

17-Propyl-1,14-dihydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reaction of 17-propyl-1-hydroxy-14-triisopropylsilyloxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in acetonitrile and aqueous 48% hydrofluoric acid as in Example 53 yields 17-propyl-1,14-dihydroxy-12-[2'-(4''-beta-bromo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 59

17-Ethyl-1,14-dihydroxy-12-[2'-(4'''-beta-iodo-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Method A: A solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1.5 g, 1.9 mmol) in dry dimethylformamide was treated with methyltriphenoxyphosphonium iodide (1.7 g, 3.8 mmol) at RT under an $N_2$ atmosphere and stirred for 4 hr. The reaction mixture was poured into 60 ml of water and extracted with diethyl ether (3×60 ml). The combined extracts were washed 5 times with water, dried over magnesium sulfate and evaporated in vacuo at RT. The residue was chromatographed over $SiO_2$ and eluted with methylene chloride/diethyl ether (9:1) to yield 17-ethyl-1,14-dihydroxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (883 mg, 52%).

Mass Spec: $C_{48}H_{68}I_{1}NO_{11}$ (901.93) FAB+Li: 908 (M+Li) 883, 865, 564.

Method B

The reaction of 17-ethyl-1-hydroxy-14-triisopropylsilyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) and aqueous 48% hydrofluoric acid (2.2 ml) in acetonitrile (5 ml) as in Example 20 yielded 3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (7.2 mg, 6.3%).

EXAMPLE 60

17-Allyl-1,14-dihydroxy-12-[2'-(4'''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-14-triisopropyl-silyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with aqueous 48% hydrofluoric acid in acetonitrile as in Example 59B yields 17-allyl-1,14-dihydroxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 61

17-Propyl-1,14-dihydroxy-12-[2'-(4'''-beta-iodo-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Treatment of 17-propyl-1-hydroxy-14-triisopropyl-silyloxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with aqueous 48% hydrofluoric acid in acetonitrile as in Example 59B yields 17-propyl-1,14-dihydroxy-12-[2'-(4''-beta-iodo-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 62

17-Ethyl-1,14-dihydroxy-12-[2'-(4'''-fluoro-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Treatment of 17-ethyl-1-hydroxy-14-triisopropylsilyloxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with diethylaminosulfur trifluoride (DAST) in THF followed by 48% aqueous HF/acetonitrile deblocking as in Example 64, yielded 17-ethyl-1,14-dihydroxy-12-[2'-(4''-fluoro-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

Mass Spec: $C_{43}H_{68}FNO_{11}$(794.02) FAB+Li: 954 (M+Li+matrix), 800(M+Li), 564, 266.

EXAMPLE 63

17-Ethyl-1-hydroxy-12-[2'-(4"-fluoro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with diethylaminosulfur trifluoride (DAST) in THF followed by 48% aqueous HF/acetonitrile as in Example 64 yields 17-ethyl-1-hydroxy-12-[2'-(4"-fluoro-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

EXAMPLE 64

17-Allyl-1,14-dihydroxy-12-[2'-(4"-beta-fluoro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-allyl-1-hydroxy-14-triisopropylsilyloxy-12-[2'-(4"-hydroxy-3"-methoxycyclohexyl)-1'-methylvinyl]-23,25-dimethoxy-13,19-21,27-tetramethyl-11,28-dioxa-4-azatricyclo[22.3.1.0$^{4,9}$]-octacos-18-ene-2,3,10,16-tetraone (1.68 g, 1.75 mmol) in MeCl$_2$ (20 ml) at RT was treated with diethylaminosulfur trifluroide (0.976 mg, 6.06 mmol). After 15 min at 0° C., the reaction mixture was poured into saturated NaHCO$_3$. The organic layer was separated and the aqueous layer was reextracted with MeCl$_2$. The combined organic extracts were washed with brine, dried over magnesium sulfate and evaporated in vacuo to yield crude difluorinated product. The residue was partially purified by passing over SiO$_2$ (140 gm) and eluted with a mixture of methlene chloridemethanol (100:1) to yield 755 mg of product. The material was dissolved in acetonitrile (75 ml) and treated with 48% aqueous hydrofluoric acid (23.5 ml). After 5 hours at RT, the reaction mixture was poured in water and solid NaHCO$_3$ and extracts were washed with brine, dried over magnesium sulfate and evaporated in vacuo to yield crude fluorinated product. The product was purified by preparative high pressure liquid chromatography on a partisil ODS-3 column at 60° C. Elution with acetonitrile-0.1% phosphoric acid mixtures (65-85% gradient) yielded 17-allyl-1,14-dihydroxy-12-[2'-(4"-beta-fluoro-3"-methoxycyclo-hexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone.

Mass Spec: C$_{44}$H$_{68}$FNO$_{11}$ (806.03) FAB+Li:966 (M+Li+matrix), 812 (M+Li), 600, 601, 576, 547.

EXAMPLE 65

17-Allyl-1-hydroxy-12-[2'-(4"-fluoro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-allyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with diethylaminosulfur trifluoride (DAST) in THF followed by 48% aqueous HF/acetonitrile as in Example 62 yields 17-Allyl-1-hydroxy-12-[2'-(4"-fluoro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 66

17-Ethyl-1-hydroxy-14-triisopropylsilyloxy-12-[2'-3", 4"-di-triisopropylsilyloxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(3",4"-dihydroxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (93.5 g, 4.49 mmol) and 2,6-lutidine (2.39 g, 22.3 mmol) in MeCl$_2$ (60 ml), at 0° C., was treated with triisopropylsilyl triflate (7.18 g, 23.4 mmol). After stirring at RT for 16 hr, the reaction mixture was diluted to 250 ml with n-hexane and passed over SiO$_2$ (360 g). Elution with n-hexane/ethyl acetate (3:1) yielded 17-ethyl-1-hydroxy-14-triisopropylsilyloxy-12-[2'-(3",4"-di-triisopropylsilyloxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5.45 g, 97%).

EXAMPLE 67

17-Ethyl-1-hydroxy-14-triisopropylsilyloxy-1 2-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-ethyl-1-hydroxy-14-triisopropylsilyloxy-12-[2'-(3",4"-di-triisopropylsilyloxy)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone (5.2 g, 4.17 mmol) was added to a solution of p-toluenesulfonic acid monohydrate (0.263 g) in MeOH (63 ml). After stirring at RT for 18 hr, the reaction mixture was poured into saturated aqueous sodium bicarbonate and extracted with three portions of ethyl acetate. The combined extracts were washed with brine and dried over magnesium sulfate. The solvent was removed in vacuo and the residue was chromatographed over SiO$_2$ (180 g). Elution with n-hexane/ethyl acetate (1:3) yielded 17-ethyl-1-hydroxy-14-triisopropylsilyloxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.63 g, 68%).

EXAMPLE 68

17-Ethyl-1-hydroxy-14-triisopropylsilyloxy-12-[2'-(3'-'-t-butyldimethylsilyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone AND 17-Ethyl-1-hydroxy-14-triisopropylsilyloxy-12-[2'-(3"--hydroxy-4"-t-butyldimethylsilyloxycyclohexyl)-1'-methylvinyl]-23,25-dimethoxy-13,19,21,27-tetramethyl-11,28-dioxa-4-azatricyclo[22.3.1.$^{4,9}$]octacos-18-ene-2,3,10,16-tetraone A solution of 17-ethyl-1-hydroxy-14-triisopropylsilyloxy-12-[2'-(3",4"-di-hydroxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene-2,3,10,16-tetraone (80.9 gm, 8.65 mmol) in mixture of dimethylformamide (60 ml) and methylene chloride (30 ml) and imidazole (1.77 g) under N$_2$ atmosphere was treated with t-butyldimethylsilyl chloride 1.74 g 11.55 mol). After stirring at RT for 16 hrs, the reaction mixture was poured into water (600 ml) and resultant suspension was extracted with ether. The combined extracts were washed with water (5 times), dried over magnesium sulfate and evaporated in vacuo. The residue was chromatographed over SiO$_2$. Elution with methylene chloride-ethyl ether (100:10) yielded 1 7-Ethyl-1-hydroxy-14-triisopropylsilyloxy-12-[2'-(3"-t-butyldimethylsilyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (1.71 g, 17%, rf=0.66), 17-ethyl--1-hydroxy-14-triisopropylsilyoxy-12-[2'-(3"-t-butyld imethylsilyl-4"-hydroxycyclohecyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1.82 gm, rf=0.41) and 17-ethyl-1-hydroxy-14-triisopropylsilyloxy-12-[2'-(3"-hydroxy-4"-t-butyldimethylsilyloxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (1.67 gm, rf=0.31).

EXAMPLE 69

17-Ethyl-1-hydroxy-14-triisopropylsilyloxy-12-[2'-(3'-'-t-butyldimethylsilyloxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(3"-t-butyldimethylsilyl-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (283 mg, 0.269 mmol) in ethyl ether (10 ml) and boron trifluoride etherate (0.04 ml) is treated with an excess of freshly prepared ethereal solution of diazomethane. After 30 min at RT, the reaction mixture is washed with sat'd. NaHCO$_3$ and brine. After drying over magnesium sulfate, the solvent is removed in vacuo. The residue is chromatographed over SiO$_2$ and eluted with n-hexane-ethyl acetate (3:1) to yield 17-ethyl-1-hydroxy-14-triisopropylsilyloxy-12-[2'-(3"-t-butyldimethylsilyloxy-4"-methoxycyclohexyl)-1-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 70

17-Ethyl-1-hydroxy-14-triisopropylsilyloxy-12-[2'-(3"-hydroxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-14-triisopropylsilyloxy-12-[2'-(3"-t-butyldimethylsilyloxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is treated with p-toluenesulfonic in methanol as in Example 67 to yield 17-ethyl-1-hydroxy-14-triisopropylsilyloxy-12-[2'-(3"-hydroxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 71

17-Ethyl-1-hydroxy-14-triisopropylsilyloxy-12-[2'-(-3"-o-nitrobenzenesulfonyloxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reaction of 17-ethyl-1-hydroxy-14-triisopropylsi lyloxy-12-[2'-(3"-hydroxy-4"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with o-nitrobenzenesulfonyl chloride as in Example 34 yields 17-ethyl-1-hydroxy--14-triisopropylsilyloxy-12-[2'-(3"-o-nitr obenzenesulfonyloxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

EXAMPLE 72

17-Ethyl-1-hydroxy-14-triisopropylsilyloxy-12-[2'-(3"-alpha-chloro-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy--14-triisopropylsilyloxy-12-[2'-(3"-o-nitr obenzenesulfonyloxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is treated with lithium chloride as in Example 36 to yield 17-ethyl-1-hydroxy-14-triisopropylsilyloxy-12-[2'-(3" -alpha-chloro-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 73

17-Ethyl-1-hydroxy-14-triisopropylsilyloxy-12-[2'-(3"-alpha-bromo-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy--14-triisopropylsilyloxy-12-[2'-(3"-o-nitr obenzenesulfonyloxy-4"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is treated with lithium bromide as in Example 42 to yield 17-ethyl-1-hydroxy-14-triisopropylsilyloxy-12-[2'-(3" -alpha-bromo-4"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

EXAMPLE 74

17-Ethyl-1-hydroxy-14-triisopropylsilyloxy-12-[2'-(3''-alpha-iodo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The reaction of 17-ethyl-1-hydroxy-14-triisopropylsilyloxy-12-[2'-(3''-hydroxy-4''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone with methyltriphenoxyphosphonium iodide as in Example 49 yields 17-ethyl-1-hydroxy-14-triisopropylsilyloxy-12-[2'-(3''-alpha-iodo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 75

17-Ethyl-1,14-dihydroxy-12-[2'-(3''-alpha-chloro-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-Ethyl-1-hydroxy-14-triisopropylsilyloxy-12-[2'-(3''-alpha-chloro-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is treated with 48% hydrofluoric acid in acetonitrile as in Example 54 to yield 17-Ethyl-1,14-dihydroxy-12-[2'-(3''-alpha chloro-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 76

17-Ethyl-1,14-dihydroxy-12-[2'-(3''-alpha-bromo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1-hydroxy-14-triisopropylsilyloxy-12-[2'-(3''-alpha-bromo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with 48% aqueous hydrofluoric acid in acetonitrile as in Example 54 yields 17-Ethyl-1,14-dihydroxy-12-[2'-(3''-alpha-bromo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 77

17-Ethyl-1,14-dihydroxy-12-[2'-(3''-alpha-iodo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of 17-ethyl-1-hydroxy-14-triisopropylsilyloxy-12-[2'-(3''-alpha-iodo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone with 48% aqueous hydrofluoric acid in acetonitrile as in Example 54 yields 17-Ethyl-1,14--dihydroxy-12-[2'-(3'-alpha-iodo-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 78

17-Ethyl-1-hydroxy-12-[2'-(4''-t-butyldimethylsilyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetra one (0.777 g, 1.0 mmol) in anhydrous CH$_2$Cl$_2$ (7.0 ml) and anhydrous dimethylformamide (3 ml) was treated with imidazole (204 mg, 3.0 mmol) and t-butyldimethylsilyl chloride (226 mg, 1.5 mmol). The reaction mixture was stirred at RT for 16 hr and diluted with H$_2$O (50 ml). The aqueous layer was separated and extracted with additional CH$_2$Cl$_2$. The combined organic extracts were washed with brine and dried over magnesium sulfate. The solvent was removed in vacuo and the residue chromatographed over SiO$_2$. Elution with n-hexane/ethyl acetate yielded a mixture of 17-ethyl-1-hydroxy-12-[2'-(3''-t-butyldimethylsilyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 17-ethyl-1-hydroxy-12-[2'-(4''-t-butyldimethylsilyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 79

17-Ethyl-1-hydroxy-12-[2'-(3''-t-butyldimethylsilyloxy,4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone An ethereal solution of 17-ethyl-1-hydroxy-12-[2'-(3'-t-butyldimethylsilyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is treated with diazomethane and BF$_3$ etherate as in Example 67 to yield 17-ethyl-1-hydroxy-12-[2'-(3''-t-butyldimethylsilyloxy-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 80

17-Ethyl-1-hydroxy-12-[4''-methoxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone AND 17-Ethyl-1-hydroxy-12-[2'-(3''-methoxy-4''methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Treatment of a methanolic solution of 17-ethyl-1-hydroxy-12-[2'-(3''-t-butyldimethylsilyloxy-4''-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone with p-toluenesulphonic acid as in Example 7 yields 17 ethyl-1-hydroxy-12-[2'-(3''-hydroxy-4''-methoxycyclohexyl)-1'-methylvinyl]-23,25-dimethoxy-13,19,21,27- tetramethyl-11,28-dioxa-4-azatricyclo-[22.3.1.0$^{4,9}$]-octacos-18-ene-2,3,10,16-tetraone.

EXAMPLE 81

17-Ethyl-1-hydroxy-12-[2'-(4''-fluoro-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(3''-hydroxy-4''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in MeCl$_2$ is treated with diethylaminosulfur triflouride and the resultant product is treated with 48% aqueous hydrofluoric acid as in Example 63 yields 17-ethyl-1-hydroxy-12-[2'-(3''-fluoro-4''-methoxycyclohexyl)-1'-methylvinyl]-23,25-dimethoxy-13,19,21,27-tetrmethyl-11,28,dioxa-4-azatricyclo[22.3.1.0$^{4,9}$]octacos-18-ene-2,3,10,16-tetraone.

EXAMPLE 82

17-Ethyl-1-hydroxy-12-[2'-(4''-o-nitrobenzenesulfonyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone(1) and
17-Ethyl-1-hydroxy-12-[2'-(3''-o-nitrobenzenesulfonyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone(2)

To a solution of 17-ethyl-1-hydroxy-12-[2'-(3'',4'''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg) in dry methylene chloride (20 mL) was added diisopropylethylamine (150 μl) followed by o-nitrobenzenesulfonyl chloride (60 mg), then dimethylaminopyridine (27 mg). The yellow solution was stirred at room temperature under nitrogen atmosphere for 4 hour and quenched with sat'd aqueous sodium bicarbonate. Organic layer was washed (water, sat'd NaHCO$_3$, sat'd NaCl), dried (anhydrous Na$_2$SO$_4$) and the solvent was removed in vacuo. Chromatography on silica gel (2:1 ethyl acetate:hexane) gave 70 mg of the title compound 1 and 60 mg of the titled compound 2 (Mass Spec: $^1$H and $^{13}$C NMR data are consistent with the proposed structures).

EXAMPLE 83

17-Ethyl-1-hydroxy-12-[2'-(3''(R),4''(S)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone To a solution of 17-ethyl-1-hydroxy-12-[2'-(4''-o-nitrobenzenesulfonyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone (60 mg) in 3 ml of dry methylene chloride was added triethylamine (1 ml) under nitrogen atmosphere and stirred at room temperature for three days. The solvent was removed under reduced pressure and the residue was purified by column chromatography on silica gel (2:3 n-hexane:ethyl acetate) to give 42 mg of the titled compound.

Mass Spec: 744 (M+H$^+$), 766 (M+Na)

EXAMPLE 84

17-Ethyl-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone The title compound was prepared by the method of Example 83 utilizing 17-ethyl-1-hydroxy-12-[2'(3''-o-nitrobenzenesulfonyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 85

17-Ethyl-1-hydroxy-12-[2'-(3''-chloro-4''-trimethylsilyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg) in 1.5 ml of methylene chloride was added 200 μl of trimethylsilyl azide followed by a solution of titanium chloride in methylene chloride (20 μl, 1 mole solution) at room temperature under nitrogen atmosphere. The reaction mixture was stirred at this temperature overnight and the light yellow mixture was purified on preparative tlc on silica gel (2:1 hexane:ethyl acetate) to give 32 mg of the title compound.

Mass Spec: 858 (M+Li)

EXAMPLE 86

17-Ethyl-1-hydroxy-12-[2'-(4''-chloro-3''-trimethylsilyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 85 utilizing 17-ethyl-1-hydroxy-12-[2'-(3''(R),4''(S)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 87

17-Ethyl-1-hydroxy-12-[2'-(3''-chloro-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3''-chloro-4''-trimethylsilyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg) in 1 ml of methylene chloride was added a solution of p-toluenesulfonic acid (200 μl, 1% solution in methanol) and stirred for 20 minutes at room temperature. Purification of the crude product by preparative tlc on silica gel (1:1 hexane:ethyl acetate) gave the title compound in quantitative yield.

Mass Spec: 762 (M+Li)

EXAMPLE 88

17-Ethyl-1-hydroxy-12-[2'-[4''-chloro-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 87 utilizing 17-ethyl-1-hydroxy-12-[2'-(4''-chloro-3''-trimethylsilyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 89

17-Ethyl-1-hydroxy-12-[2'-(3''-bromo-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A suspension of lithium bromide (181 mg) in dry benzene (2.2 ml) with hexamethylphosphoramide (350 μl) was sonicated for 45 minutes. 500 μl of this mixture was added to a solution of 17-ethyl-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (63 mg) in 100 μl of benzene. The reaction mixture was heated at 50° C. under nitrogen atmosphere for 30 minutes and cooled to room temperature. Purification of the crude material on preparative tlc on silica gel (2:1 hexane:ethyl acetate) gave 18 mg of the title compound.
Mass Spec: 830/832 (M+Li).

EXAMPLE 90

17-Ethyl-1-hydroxy-12-[2'-(4''-bromo-3''-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound was prepared by the method of Example 89 utilizing 17-ethyl-1-hydroxy-12-[2'-(3''(R),4''(S)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as a starting material.

EXAMPLE 91

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspened in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 ul/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radio activity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The concentration of compound required to inhibit the proliferation of T-cells by 50% was measured, and the results were as follows:

| Example No. Of Product Compound | IC$_{50}$ (M) |
| --- | --- |
| 40 | $<1 \times 10^{-6}$ |
| 53 | $<1 \times 10^{-6}$ |
| 56 | $<1 \times 10^{-6}$ |
| 59 | $<1 \times 10^{-6}$ |
| 62 | $<1 \times 10^{-6}$ |
| 87 | $<1 \times 10^{-6}$ |
| 89 | $<1 \times 10^{-6}$ |

While the foregoing specifications teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

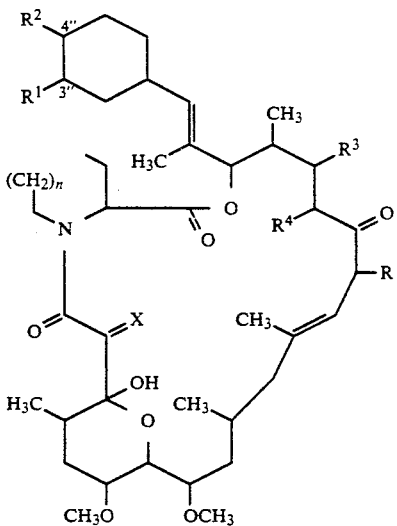

wherein:
R is methyl, ethyl, propyl or allyl;
R[1] and R[2] are independently halo, hydroxy, and $C_1$-$C_8$ alkoxy, with the proviso that at least one R[1] or R[2] is halogen; R[3] is hydrogen or hydroxy and R[4] is hydrogen; or R[3] and R[4] can be taken together to form a double bond; X=O or (HO, H) and n is 1 or 2.

2. A compound according to claim 1 wherein the steric configuration of formula I is as defined in the following formula XV:

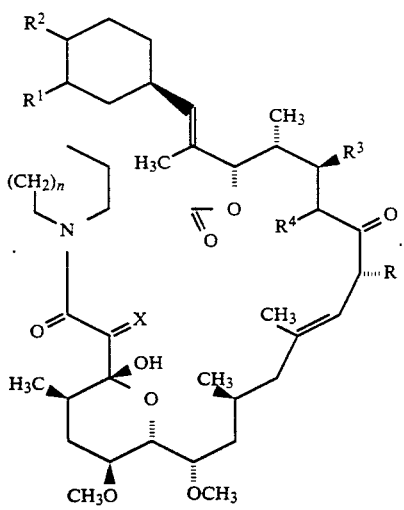

3. The compound of claim 1 being:
17-Ethyl-1,14-dihydroxy-12-[2'-(4"-beta-bromo-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-beta-iodo-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-beta-chloro-3"-methoxycyclohexyl)-1'-methylvinyl]-23,25-dimethoxy-13,19,21,-27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-fluoro-3"-methoxycyclohexyl)-1'-methylvinyl]-23,25-dimethoxy-13,19,21,-27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"'-beta-chloro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"'-beta-bromo-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"'-beta-iodo-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"'-fluoro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4"'-beta-chloro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4"'-beta-bromo-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4"'-beta-iodo-3"-methoxycyclohexyl)-1'-methylvinyl]-23,25-dimethoxy-13,19,21,27-tetramethyl-11,28-dioxa-4-azatri-cyclo[22.3.1.0$^{4,9}$]octacos-18-ene-2,3,10,16-tetraone;

17-Allyl-1,14-dihydroxy-12-[2'-4"-fluoro-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-alpha-bromo-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-hydroxy-3"-beta-chlorocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-alpha-chloro-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-hydroxy-3"-beta-bromocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1-hydroxy-12-[2'-(4"-alpha-chloro-3"-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-propyl-1-hydroxy-12-[2'-(4''-hydroxy-3''-betachlorocyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone.

4. The compound of claim 1 which is:

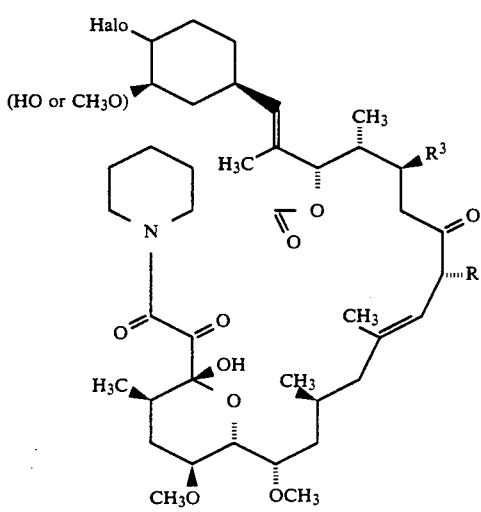

wherein halo is F, Cl, Br or I; $R^3$ is hydrogen or hydroxy, and R is ethyl, propyl or allyl.

5. The compound of claim 1 which is:

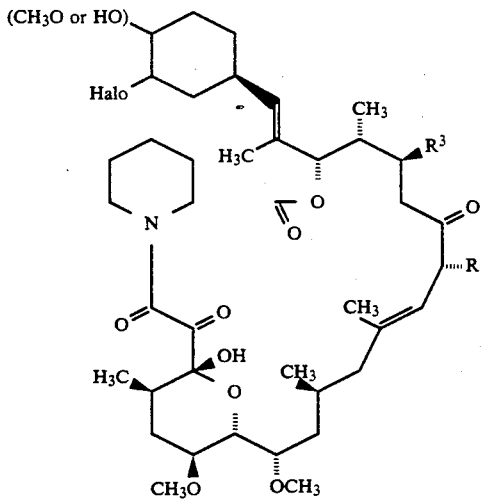

where halo is F, Cl, Br, or I; $R^3$ is hydrogen or hydroxyl and R is ethyl, propyl or allyl.

6. A pharmaceutical composition for the treatment of immunoregulatory disorders or diseases comprising a pharmaceutical carrier and a therapeutically effective amount of compound of formula I, according to claim 1.

7. A pharmaceutical composition for the topical treatment of inflammatory and hyper-proliferative skin diseases and or cutaneous manifestations of immunologically-mediated illnesses comprising a pharmaceutical carrier and a therapeutically effective amount of compound of formula I, according to claim 1.

8. A method for the treatment of immunoregulatory disorders or diseases comprising the administration to a mammalian species in need of such treatment an effective amount of a compound of formula I according to claim 1.

9. A method for the topical treatment of inflammatory and hyperproliferative skin diseases and or cutaneous manifestations of immunologically-mediated illnesses comprising the administration to a mammalian species in need of such treatment an effective amount of a compound of formula I according to claim 1.

* * * * *